US011364340B2

(12) United States Patent
Rosinko

(10) Patent No.: US 11,364,340 B2
(45) Date of Patent: *Jun. 21, 2022

(54) SIMPLIFIED INSULIN PUMP FOR TYPE II DIABETICS

(71) Applicant: Tandem Diabetes Care, Inc., San Diego, CA (US)

(72) Inventor: Mike Rosinko, Anaheim, CA (US)

(73) Assignee: Tandem Diabetes Care, Inc., San Diego, CA (US)

(*) Notice: Subject to any disclaimer, the term of this patent is extended or adjusted under 35 U.S.C. 154(b) by 654 days.

This patent is subject to a terminal disclaimer.

(21) Appl. No.: 16/269,767

(22) Filed: Feb. 7, 2019

(65) Prior Publication Data

US 2019/0167901 A1 Jun. 6, 2019

Related U.S. Application Data

(63) Continuation of application No. 13/800,595, filed on Mar. 13, 2013, now Pat. No. 10,201,656.

(51) Int. Cl.
*A61M 5/172* (2006.01)
*A61M 5/142* (2006.01)

(52) U.S. Cl.
CPC ........ *A61M 5/172* (2013.01); *A61M 5/14244* (2013.01); *A61M 5/1723* (2013.01); *A61M 2005/14208* (2013.01); *A61M 2205/18* (2013.01); *A61M 2205/505* (2013.01)

(58) Field of Classification Search
CPC .............. A61M 5/172; A61M 5/14244; A61M 5/1723; A61M 2005/14208; A61M 2205/18; A61M 2205/505
See application file for complete search history.

(56) References Cited

U.S. PATENT DOCUMENTS

| 2,462,596 A | 2/1949 | Bent |
| 2,629,376 A | 2/1953 | Pierre et al. |
| 2,691,542 A | 10/1954 | Chenoweth |
| 3,059,639 A | 10/1962 | Blackman et al. |
| 4,469,481 A | 9/1984 | Kobayashi |
| 5,395,326 A | 3/1995 | Haber et al. |

(Continued)

FOREIGN PATENT DOCUMENTS

| DE | 399065 C | 7/1924 |
| DE | 19819407 A1 | 11/1999 |

(Continued)

OTHER PUBLICATIONS

Application and File History for U.S. Appl. No. 13/800,595, filed Mar. 13, 2013, inventors Saint.

(Continued)

*Primary Examiner* — Theodore J Stigell
(74) *Attorney, Agent, or Firm* — Patterson Thuente Pedersen, P.A.

(57) ABSTRACT

A simplified insulin pump allows type II diabetics to identify routine patterns in their daily lifestyle that provide a generally accurate typical pattern of activity and meals. An infusion regimen can be programmed into the pump that generally correlates with this typical pattern to provide a viable treatment option for a type II diabetic without the need for specific and precise matching of insulin to carbohydrate consumption or activity level.

20 Claims, 4 Drawing Sheets

(56) References Cited

U.S. PATENT DOCUMENTS

| | | |
|---|---|---|
| 5,919,216 A | 7/1999 | Houben et al. |
| 6,034,054 A | 3/2000 | Defelippis et al. |
| 6,471,689 B1 | 10/2002 | Joseph et al. |
| 6,544,212 B2 | 4/2003 | Galley et al. |
| 6,551,276 B1 | 4/2003 | Mann et al. |
| 6,551,992 B1 | 4/2003 | Defelippis et al. |
| 6,554,798 B1 | 4/2003 | Mann et al. |
| 6,558,351 B1 | 5/2003 | Steil et al. |
| 6,562,001 B2 | 5/2003 | Lebel et al. |
| 6,571,128 B2 | 5/2003 | Lebel et al. |
| 6,572,542 B1 | 6/2003 | Houben et al. |
| 6,577,899 B2 | 6/2003 | Lebel et al. |
| 6,648,821 B2 | 11/2003 | Lebel et al. |
| 6,668,196 B1 | 12/2003 | Villegas et al. |
| 6,740,072 B2 | 5/2004 | Starkweather et al. |
| 6,740,075 B2 | 5/2004 | Lebel et al. |
| 6,744,350 B2 | 6/2004 | Blomquist |
| 6,810,290 B2 | 10/2004 | Lebel et al. |
| 6,827,702 B2 | 12/2004 | Lebel et al. |
| 6,852,104 B2 | 2/2005 | Blomquist |
| 6,862,466 B2 | 3/2005 | Ackerman |
| 6,872,200 B2 | 3/2005 | Mann et al. |
| 6,873,268 B2 | 3/2005 | Lebel et al. |
| 6,906,028 B2 | 6/2005 | Defelippis et al. |
| 6,936,029 B2 | 8/2005 | Mann et al. |
| 6,958,705 B2 | 10/2005 | Lebel et al. |
| 6,974,437 B2 | 12/2005 | Lebel et al. |
| 6,979,326 B2 | 12/2005 | Mann et al. |
| 6,997,920 B2 | 2/2006 | Mann et al. |
| 6,998,387 B1 | 2/2006 | Goke et al. |
| 6,999,854 B2 | 2/2006 | Roth |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,109,878 B2 | 9/2006 | Mann et al. |
| 7,204,823 B2 | 4/2007 | Estes et al. |
| 7,258,864 B2 | 8/2007 | Clark |
| 7,267,665 B2 | 9/2007 | Steil et al. |
| 7,354,420 B2 | 4/2008 | Steil et al. |
| 7,402,153 B2 | 7/2008 | Steil et al. |
| 7,442,186 B2 | 10/2008 | Blomquist |
| 7,497,827 B2 | 3/2009 | Brister et al. |
| 7,510,544 B2 | 3/2009 | Vilks et al. |
| 7,515,060 B2 | 4/2009 | Blomquist |
| 7,517,530 B2 | 4/2009 | Clark |
| 7,547,281 B2 | 6/2009 | Hayes et al. |
| 7,569,030 B2 | 8/2009 | Lebel et al. |
| 7,572,789 B2 | 8/2009 | Cowen et al. |
| 7,642,232 B2 | 1/2010 | Green et al. |
| 7,651,489 B2 | 1/2010 | Estes et al. |
| 7,674,485 B2 | 3/2010 | Bhaskaran et al. |
| 7,678,071 B2 | 3/2010 | Lebel et al. |
| 7,678,762 B2 | 3/2010 | Green et al. |
| 7,678,763 B2 | 3/2010 | Green et al. |
| 7,704,226 B2 | 4/2010 | Mueller, Jr. et al. |
| 7,711,402 B2 | 5/2010 | Shults et al. |
| 7,734,323 B2 | 6/2010 | Blomquist et al. |
| 7,751,907 B2 | 7/2010 | Blomquist |
| 7,756,722 B2 | 7/2010 | Levine et al. |
| 7,766,831 B2 | 8/2010 | Essenpreis et al. |
| 7,780,981 B2 | 8/2010 | Dipierro et al. |
| 7,785,313 B2 | 8/2010 | Mastrototaro |
| 7,806,886 B2 | 10/2010 | Kanderian, Jr. et al. |
| 7,815,602 B2 | 10/2010 | Mann et al. |
| 7,819,843 B2 | 10/2010 | Mann et al. |
| 7,831,310 B2 | 11/2010 | Lebel et al. |
| 7,837,647 B2 | 11/2010 | Estes et al. |
| 7,850,641 B2 | 12/2010 | Lebel et al. |
| 7,905,859 B2 | 3/2011 | Bynum et al. |
| 7,920,907 B2 | 4/2011 | McGarraugh et al. |
| 7,976,870 B2 | 7/2011 | Berner et al. |
| 8,012,119 B2 | 9/2011 | Estes et al. |
| 8,062,249 B2 | 11/2011 | Wilinska et al. |
| 8,105,268 B2 | 1/2012 | Lebel et al. |
| 8,119,593 B2 | 2/2012 | Richardson et al. |
| 8,133,197 B2 | 3/2012 | Blomquist et al. |
| 8,152,789 B2 | 4/2012 | Starkweather et al. |
| 8,206,350 B2 | 6/2012 | Mann et al. |
| 8,208,984 B2 | 6/2012 | Blomquist et al. |
| 8,219,222 B2 | 7/2012 | Blomquist |
| 8,221,345 B2 | 7/2012 | Blomquist |
| 8,250,483 B2 | 8/2012 | Blomquist |
| 8,257,300 B2 | 9/2012 | Budiman et al. |
| 8,287,487 B2 | 10/2012 | Estes |
| 8,287,495 B2 | 10/2012 | Michaud et al. |
| 8,298,184 B2 | 10/2012 | Diperna et al. |
| 8,311,749 B2 | 11/2012 | Brauker et al. |
| 8,337,469 B2 | 12/2012 | Eberhart et al. |
| 8,344,847 B2 | 1/2013 | Moberg et al. |
| 8,346,399 B2 | 1/2013 | Blomquist |
| 8,348,886 B2 | 1/2013 | Kanderian, Jr. et al. |
| 8,348,923 B2 | 1/2013 | Kanderian, Jr. et al. |
| 8,414,523 B2 | 4/2013 | Blomquist et al. |
| 8,454,510 B2 | 6/2013 | Yodfat et al. |
| 8,454,576 B2 | 6/2013 | Mastrototaro et al. |
| 8,454,581 B2 | 6/2013 | Estes et al. |
| 8,465,460 B2 | 6/2013 | Yodfat et al. |
| 8,573,027 B2 | 11/2013 | Rosinko et al. |
| 8,657,779 B2 | 2/2014 | Blomquist |
| 8,712,748 B2 | 4/2014 | Thukral |
| 8,753,316 B2 | 6/2014 | Blomquist |
| 8,775,877 B2 | 7/2014 | McVey et al. |
| 8,882,701 B2 | 11/2014 | Debelser et al. |
| 8,938,306 B2 | 1/2015 | Lebel |
| 8,986,253 B2 | 3/2015 | Diperna |
| 8,992,475 B2 | 3/2015 | Mann |
| 9,008,803 B2 | 4/2015 | Blomquist |
| 9,114,210 B2 | 8/2015 | Estes |
| 9,474,856 B2 | 10/2016 | Blomquist |
| 9,492,608 B2 | 11/2016 | Saint |
| 9,603,995 B2 | 3/2017 | Rosinko et al. |
| 9,737,656 B2 | 8/2017 | Blomquist |
| 9,940,441 B2 | 4/2018 | Walsh |
| 10,016,561 B2 | 7/2018 | Saint et al. |
| 10,049,768 B2 | 8/2018 | Blomquist |
| 10,201,656 B2 * | 2/2019 | Rosinko ............... A61M 5/172 |
| 2002/0016568 A1 | 2/2002 | Lebel |
| 2002/0019606 A1 | 2/2002 | Lebel |
| 2002/0065454 A1 | 5/2002 | Lebel |
| 2002/0107476 A1 | 8/2002 | Mann |
| 2003/0055406 A1 | 3/2003 | Lebel |
| 2003/0065308 A1 | 4/2003 | Lebel et al. |
| 2003/0163088 A1 | 8/2003 | Blomquist |
| 2003/0163223 A1 * | 8/2003 | Blomquist .......... A61M 5/1723 700/282 |
| 2003/0163789 A1 | 8/2003 | Blomquist |
| 2003/0212364 A1 | 11/2003 | Mann et al. |
| 2004/0193090 A1 | 9/2004 | Lebel et al. |
| 2005/0022274 A1 | 1/2005 | Campbell et al. |
| 2005/0143864 A1 | 6/2005 | Blomquist |
| 2005/0171513 A1 | 8/2005 | Mann et al. |
| 2005/0272640 A1 | 12/2005 | Doyle |
| 2006/0173406 A1 | 8/2006 | Hayes |
| 2006/0173444 A1 | 8/2006 | Choy et al. |
| 2007/0016170 A1 | 1/2007 | Kovelman |
| 2007/0033074 A1 | 2/2007 | Nitzan et al. |
| 2007/0066956 A1 | 3/2007 | Finkel |
| 2007/0112298 A1 | 5/2007 | Mueller, Jr. et al. |
| 2007/0118405 A1 | 5/2007 | Campbell et al. |
| 2007/0161955 A1 | 7/2007 | Bynum et al. |
| 2007/0287985 A1 | 12/2007 | Estes et al. |
| 2008/0033357 A1 | 2/2008 | Mann et al. |
| 2008/0071580 A1 | 3/2008 | Marcus et al. |
| 2008/0097289 A1 | 4/2008 | Steil et al. |
| 2008/0114299 A1 | 5/2008 | Damgaard-Sorensen |
| 2008/0147004 A1 | 6/2008 | Mann et al. |
| 2008/0147050 A1 | 6/2008 | Mann et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |

(56) References Cited

U.S. PATENT DOCUMENTS

| | | |
|---|---|---|
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0269714 A1 | 10/2008 | Mastrototaro et al. |
| 2008/0269723 A1 | 10/2008 | Mastrototaro et al. |
| 2008/0300534 A1 | 12/2008 | Blomquist |
| 2009/0006129 A1 | 1/2009 | Thukral |
| 2009/0036753 A1 | 2/2009 | King |
| 2009/0163855 A1 | 6/2009 | Shin et al. |
| 2009/0177142 A1 | 7/2009 | Blomquist et al. |
| 2009/0177147 A1 | 7/2009 | Blomquist et al. |
| 2009/0247931 A1 | 10/2009 | Damgaard-Sorensen |
| 2009/0275886 A1 | 11/2009 | Blomquist et al. |
| 2010/0008795 A1 | 1/2010 | Diperna |
| 2010/0094251 A1 | 4/2010 | Estes |
| 2010/0114015 A1 | 5/2010 | Kanderian, Jr. et al. |
| 2010/0125241 A1 | 5/2010 | Prud et al. |
| 2010/0145262 A1 | 6/2010 | Bengtsson et al. |
| 2010/0145303 A1 | 6/2010 | Yodfat et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0174266 A1 | 7/2010 | Estes |
| 2010/0174553 A1 | 7/2010 | Kaufman et al. |
| 2010/0185142 A1 | 7/2010 | Kamen et al. |
| 2010/0185175 A1 | 7/2010 | Kamen et al. |
| 2010/0198142 A1 | 8/2010 | Sloan et al. |
| 2010/0198520 A1 | 8/2010 | Breton et al. |
| 2010/0218132 A1 | 8/2010 | Soni et al. |
| 2010/0249530 A1 | 9/2010 | Rankers et al. |
| 2010/0249561 A1 | 9/2010 | Patek et al. |
| 2010/0262117 A1 | 10/2010 | Magni et al. |
| 2010/0262434 A1 | 10/2010 | Shaya |
| 2010/0274592 A1 | 10/2010 | Nitzan et al. |
| 2010/0280329 A1 | 11/2010 | Randloev et al. |
| 2010/0286653 A1 | 11/2010 | Kubel et al. |
| 2010/0292634 A1 | 11/2010 | Kircher, Jr. et al. |
| 2010/0305545 A1 | 12/2010 | Kanderian, Jr. et al. |
| 2010/0324382 A1 | 12/2010 | Cantwell et al. |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0021898 A1 | 1/2011 | Wei et al. |
| 2011/0033833 A1 | 2/2011 | Blomquist et al. |
| 2011/0040251 A1 | 2/2011 | Blomquist et al. |
| 2011/0054390 A1 | 3/2011 | Searle et al. |
| 2011/0054391 A1 | 3/2011 | Ward et al. |
| 2011/0071464 A1 | 3/2011 | Palerm |
| 2011/0071765 A1* | 3/2011 | Yodfat .................. G16H 15/00 702/19 |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0106011 A1 | 5/2011 | Cinar et al. |
| 2011/0106050 A1 | 5/2011 | Yodfat et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0124996 A1 | 5/2011 | Reinke et al. |
| 2011/0125095 A1 | 5/2011 | Lebel et al. |
| 2011/0130746 A1 | 6/2011 | Budiman |
| 2011/0137239 A1 | 6/2011 | Debelser et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0160695 A1 | 6/2011 | Sigrist et al. |
| 2011/0166544 A1 | 7/2011 | Verhoef et al. |
| 2011/0184264 A1 | 7/2011 | Galasso et al. |
| 2011/0196213 A1 | 8/2011 | Thukral et al. |
| 2011/0256024 A1 | 10/2011 | Cole et al. |
| 2012/0013625 A1 | 1/2012 | Blomquist et al. |
| 2012/0013802 A1 | 1/2012 | Blomquist et al. |
| 2012/0029433 A1 | 2/2012 | Michaud et al. |
| 2012/0029468 A1 | 2/2012 | Diperna |
| 2012/0030610 A1 | 2/2012 | Diperna et al. |
| 2012/0041415 A1 | 2/2012 | Estes et al. |
| 2012/0059353 A1 | 3/2012 | Kovatchev et al. |
| 2012/0220939 A1 | 8/2012 | Yodfat |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238854 A1 | 9/2012 | Blomquist |
| 2012/0265722 A1 | 10/2012 | Blomquist |
| 2012/0277667 A1 | 11/2012 | Yodat et al. |
| 2012/0302991 A1 | 11/2012 | Blomquist |
| 2012/0330227 A1 | 12/2012 | Budiman et al. |
| 2013/0046281 A1 | 2/2013 | Javitt |
| 2013/0053816 A1 | 2/2013 | Diperna et al. |
| 2013/0131630 A1 | 5/2013 | Blomquist |
| 2014/0276420 A1 | 9/2014 | Rosinko |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276574 A1 | 9/2014 | Saint |
| 2015/0182693 A1 | 7/2015 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0082188 A1 | 3/2016 | Blomquist et al. |
| 2017/0165416 A1 | 6/2017 | Saint |
| 2017/0246380 A1 | 8/2017 | Rosinko et al. |
| 2017/0312423 A1 | 11/2017 | Rosinko |
| 2018/0133397 A1 | 5/2018 | Estes |
| 2018/0133398 A1 | 5/2018 | Blomquist |
| 2018/0137252 A1 | 5/2018 | Mairs |
| 2018/0226145 A1 | 8/2018 | Walsh |
| 2018/0233221 A1 | 8/2018 | Blomquist |
| 2018/0361060 A9 | 12/2018 | Rosinko |

FOREIGN PATENT DOCUMENTS

| | | |
|---|---|---|
| WO | WO-03082091 A2 | 10/2003 |
| WO | WO-2007065944 A1 | 6/2007 |
| WO | WO-2009016636 A2 | 2/2009 |
| WO | WO-2013184896 A1 | 12/2013 |

OTHER PUBLICATIONS

International Preliminary Reporton Patentability for Application No. PCT/US2014/021075, dated Sep. 24, 2015, 12 pages.

International Search Report for Application No. PCT/US2014/021075, dated Jul. 1, 2014, 24 pages.

* cited by examiner

SIMPLIFIED INSULIN PUMP FOR TYPE II DIABETICS

RELATED APPLICATION

This application is a continuation of application Ser. No. 13/800,595 filed Mar. 13, 2013, which is hereby fully incorporated herein by reference.

FIELD OF THE INVENTION

The present invention relates to insulin pumps for the treatment of diabetes and, more particularly to a simplified insulin pump for use by Type II diabetics.

BACKGROUND

There are many applications in academic, industrial, and medical fields that benefit from devices and methods that are capable of accurately and controllably delivering fluids, such as liquids and gases that have a beneficial effect when administered in known and controlled quantities. Such devices and methods can be particularly useful in the medical field where treatments for many patients include the administration of a known amount of a substance at predetermined intervals.

Insulin-injecting pumps have been developed for the administration of insulin for those suffering from both type I and type II diabetes. Recently, continuous subcutaneous insulin injection and/or infusion therapy with portable infusion devices has been adapted for the treatment of diabetes. Such therapy may include the regular and/or continuous injection or infusion of insulin into the skin of a person suffering from diabetes, and offers an alternative to multiple daily injections of insulin by an insulin syringe or an insulin pen. Such pumps can be ambulatory/portable infusion pumps that are worn by the user and that may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference.

Current infusion pumps typically allow for delivery of two infusion types—a basal rate and a bolus delivery. A basal rate typically delivers insulin at a constant rate over an extended period of time and is provided to maintain target glucose levels throughout the day when a user is not eating. Boluses are delivered to counteract carbohydrates consumed at meal times to maintain target glucose levels. For a meal bolus, for example, the user may enter the amount of carbohydrates the user is about to ingest and the user's carbohydrate ratio (the volume of insulin programmed to be delivered for every particular number of carbohydrates predicted to be consumed by the user). Based on this information, the infusion pump will generate an estimate of a bolus amount of insulin to be delivered. If accepted by the user, e.g., by entering a command such as by depressing a button, touching an object on a touchscreen, etc., the then-current basal delivery mode is suspended and the bolus delivery is initiated.

Careful management of insulin delivery in view of carbohydrate consumption, physical activity, and other factors is critical in maintaining the health of type I diabetics. While delivery of insulin is equally important for the overall health of type II diabetics, the specific timing of the delivery and the precise matching of the amount of insulin to carbohydrates consumed is not as critical. In addition, type II diabetics are generally diagnosed only after years of not having to deal with monitoring carbohydrate intake, taking insulin injections, etc., as opposed to type I diabetics who are usually diagnosed at a much younger age. As a result of these and other factors, type II diabetics often do not have the motivation and/or the willingness to diligently monitor their carbohydrate intake, insulin levels, etc. as is required to properly use most insulin pumps.

Therefore, there is a need for an insulin pump and method that is simplified for the treatment of type II diabetics to provide a needed amount of insulin without requiring precise tracking and matching of carbohydrate intake with insulin delivered.

SUMMARY OF THE INVENTION

A simplified insulin pump allows type II diabetics to identify routine patterns in their daily lifestyle that provide a generally accurate typical pattern of activity and meals. An infusion regimen can be programmed into the pump that generally correlates with this typical pattern to provide a viable treatment option for a type II diabetic without the need for specific and precise matching of insulin to carbohydrate consumption or activity level.

In an embodiment, a portable insulin pump includes a delivery mechanism for delivering insulin to a user and a user interface to display operating parameters of the delivery mechanism and receive input from the user. A processor of the pump receives user input data defining a recurring meal bolus scheduled for delivery at a predetermined time on a type or category of day, such as a weekday. The processor provides an alert to the user through the user interface that a meal bolus is scheduled at the predetermined time on each day in the category of day and then causes the delivery mechanism to deliver the meal bolus to the user.

Certain embodiments are described further in the following description, examples, claims, and drawings. These embodiments will become more apparent from the following detailed description when taken in conjunction with the accompanying exemplary drawings.

DETAILED DESCRIPTION

Provided herein are systems, devices and methods for operating an infusion pump and particularly an insulin pump. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1:
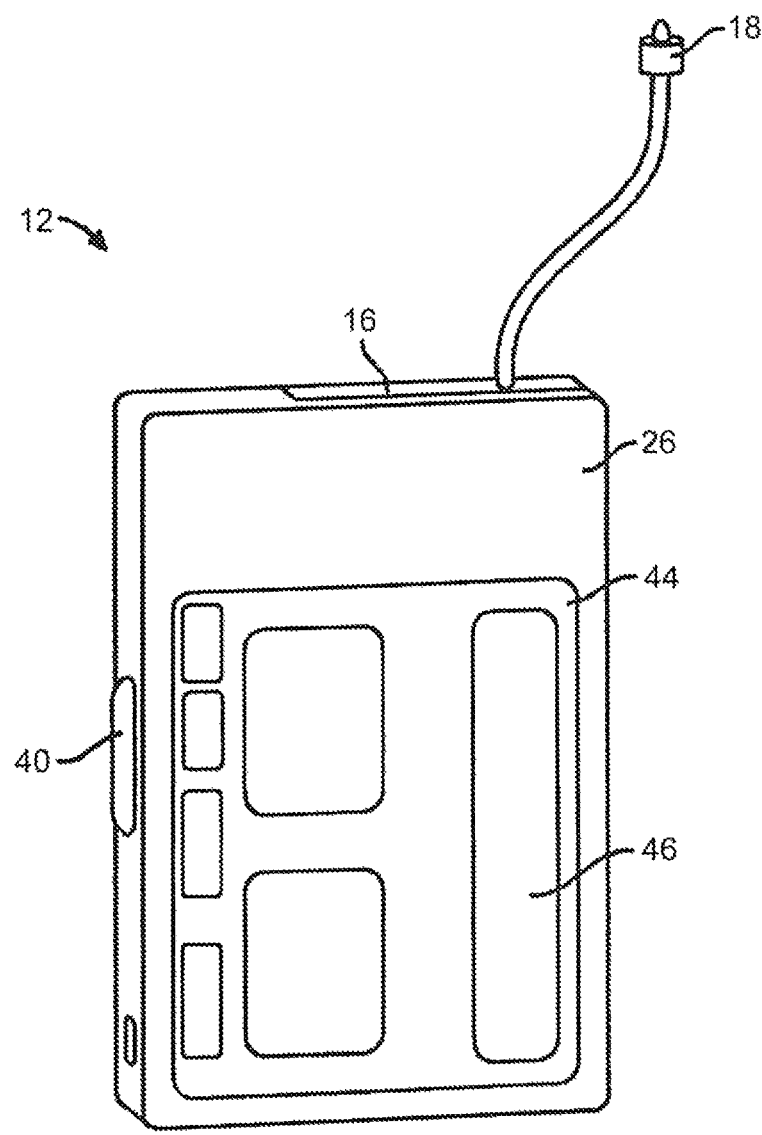
FIG. 1 is a perspective view of an infusion pump according to an embodiment of the present invention.

FIG. 1 depicts an embodiment of a pump 12 such as an infusion pump that can include an internal pumping or delivery mechanism and reservoir for delivering medicament such as insulin to a patient and an output/display 44. The type of output/display 44 may vary as may be useful for a particular application. The type of visual output/display may include LCD displays, LED displays, plasma displays, OLED displays and the like. The output/display 44 may also be an interactive or touch sensitive screen 46 having an input device such as, for example, a touch screen comprising a capacitive screen or a resistive screen. The pump 12 may additionally include a keyboard or other input device known in the art for data entry, which may be separate from the display. The output/display 44 of the pump 12 may also include a capability to operatively couple to a secondary display device such as a laptop computer, mobile communication device such as a smartphone or personal digital assistant (PDA) or the like. Further details regarding such pump devices can be found in U.S. Patent Application No. 2011/0144586, which is incorporated herein by reference.

Figure 2:
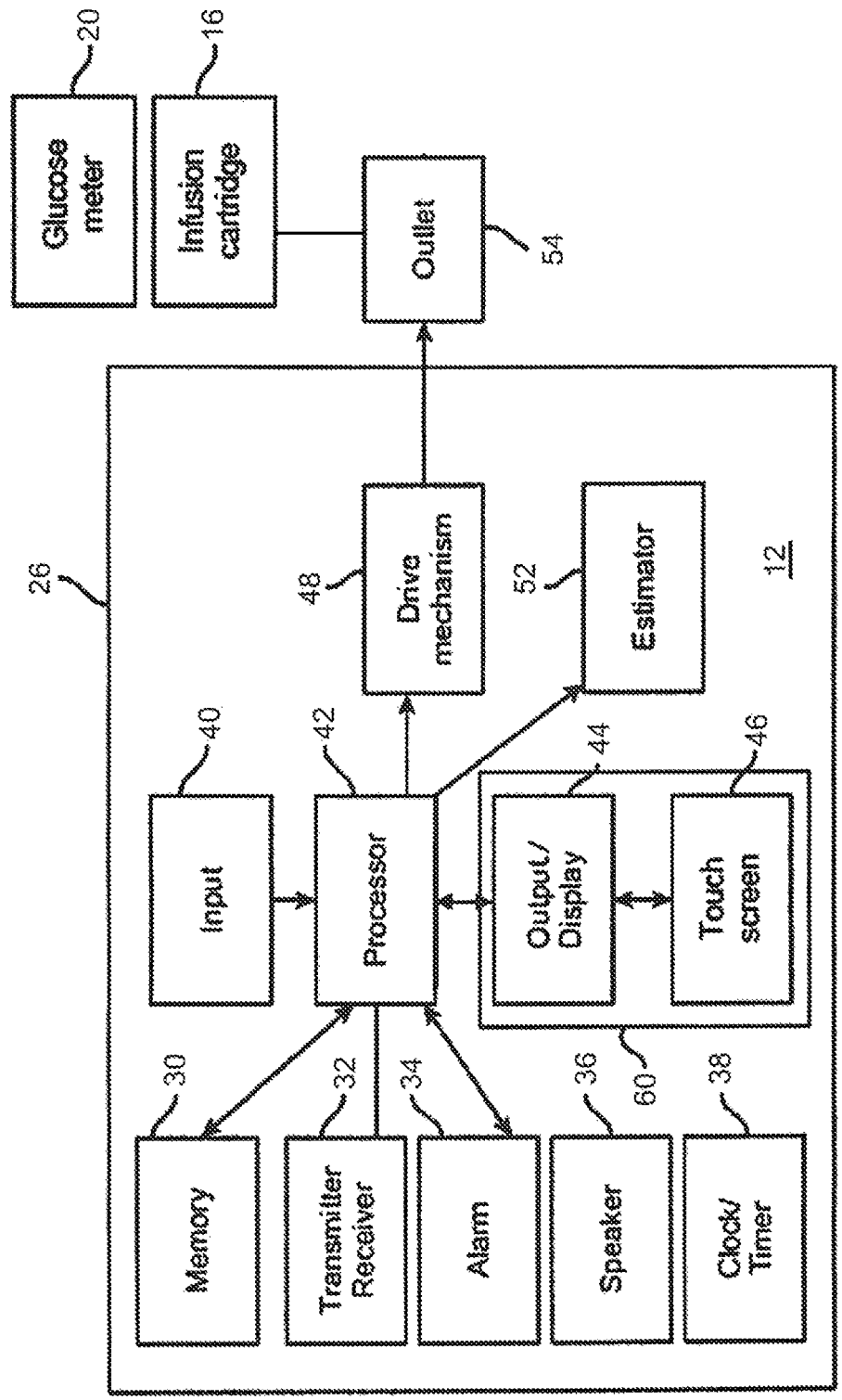
FIG. 2 is a block diagram representing an embodiment of an infusion pump.

FIG. 2 illustrates a block diagram of some of the features that may be incorporated within the housing 26 of the pump 12. The pump 12 includes a processor 42 that functions to control the overall functions of the device. The infusion pump 12 may also include a memory device 30, a transmitter/receiver 32, an alarm 34, a speaker 36, a clock/timer 38, an input device 40, the processor 42, a user interface suitable for accepting input and commands from a user such as a caregiver or patient, a drive mechanism 48, and an estimator device 52. One embodiment of a user interface as shown in FIG. 2 is a graphical user interface (GUI) 60 having a touch sensitive screen 46 with input capability. The memory device 30 may be coupled to the processor 42 to receive and store input data and to communicate that data to the processor 42. The input data may include user input data and non-user/sensor input data. The input data from the memory device 30 may be used to generate therapeutic parameters for the infusion pump 12. The GUI 60 may be configured for displaying a request for the user to input data and for receiving user input data in response to the request, and communicating that data to the memory.

The processor 42 may communicate with and/or otherwise control the drive mechanism, output/display, memory, a transmitter/receiver and other components. In some embodiments, the processor 42 may communicate with a processor of another device, for example, a continuous glucose monitor (CGM), through the transmitter/receiver. The processor 42 may include programming that can be run to control the infusion of insulin or other medicament from the cartridge, the data to be displayed by the display, the data to be transmitted via the transmitter, etc. The processor 42 may also include programming that may allow the processor to receive signals and/or other data from an input device, such as a sensor that may sense pressure, temperature or other parameters. The processor 42 may determine the capacity of the drug delivery reservoir and/or the volume of fluid disposed in the drug delivery reservoir and may set therapeutic parameters based on its determination.

The processor 42 may also include additional programming to allow the processor 42 to learn user preferences and/or user characteristics and/or user history data. This information can be utilized to implement changes in use, suggestions based on detected trends, such as, weight gain or loss. The processor can also include programming that allows the device to generate reports, such as reports based upon user history, compliance, trending, and/or other such data. Additionally, infusion pump device embodiments of the disclosure may include a "power off" or "suspend" function for suspending one or more functions of the device, such as, suspending a delivery protocol, and/or for powering off the device or the delivery mechanism thereof. For some embodiments, two or more processors may be used for controller functions of the infusion pump devices, including a high power controller and a low power controller used to maintain programming and pumping functions in low power mode, in order to save battery life.

The memory device 30 may be any type of memory capable of storing data and communicating that data to one or more other components of the device, such as the processor. The memory may be one or more of a Flash memory, SRAM, ROM, DRAM, RAM, EPROM and dynamic storage, for example. For instance, the memory may be coupled to the processor and configured to receive and store input data and/or store one or more template or generated delivery patterns. For example, the memory can be configured to store one or more personalized (e.g., user defined) delivery profiles, such as a profile based on a user's selection and/or grouping of various input factors, past generated delivery profiles, recommended delivery profiles, one or more traditional delivery profiles, e.g., square wave, dual square wave, basal and bolus rate profiles, and/or the like. The memory can also store, for example, user information, history of use, glucose measurements, compliance and an accessible calendar of events.

The housing 26 of the pump 12 may be functionally associated with an interchangeable and a removable glucose meter 20 and/or infusion cartridge 16. The infusion cartridge 16 may have an outlet port 54 that may be connected to an infusion set (not shown) via an infusion set connector 18. Further details regarding some embodiments of various infusion pump devices can be found in U.S. Patent Application No. 2011/0144586, which is hereby incorporated by reference.

Figure 3:
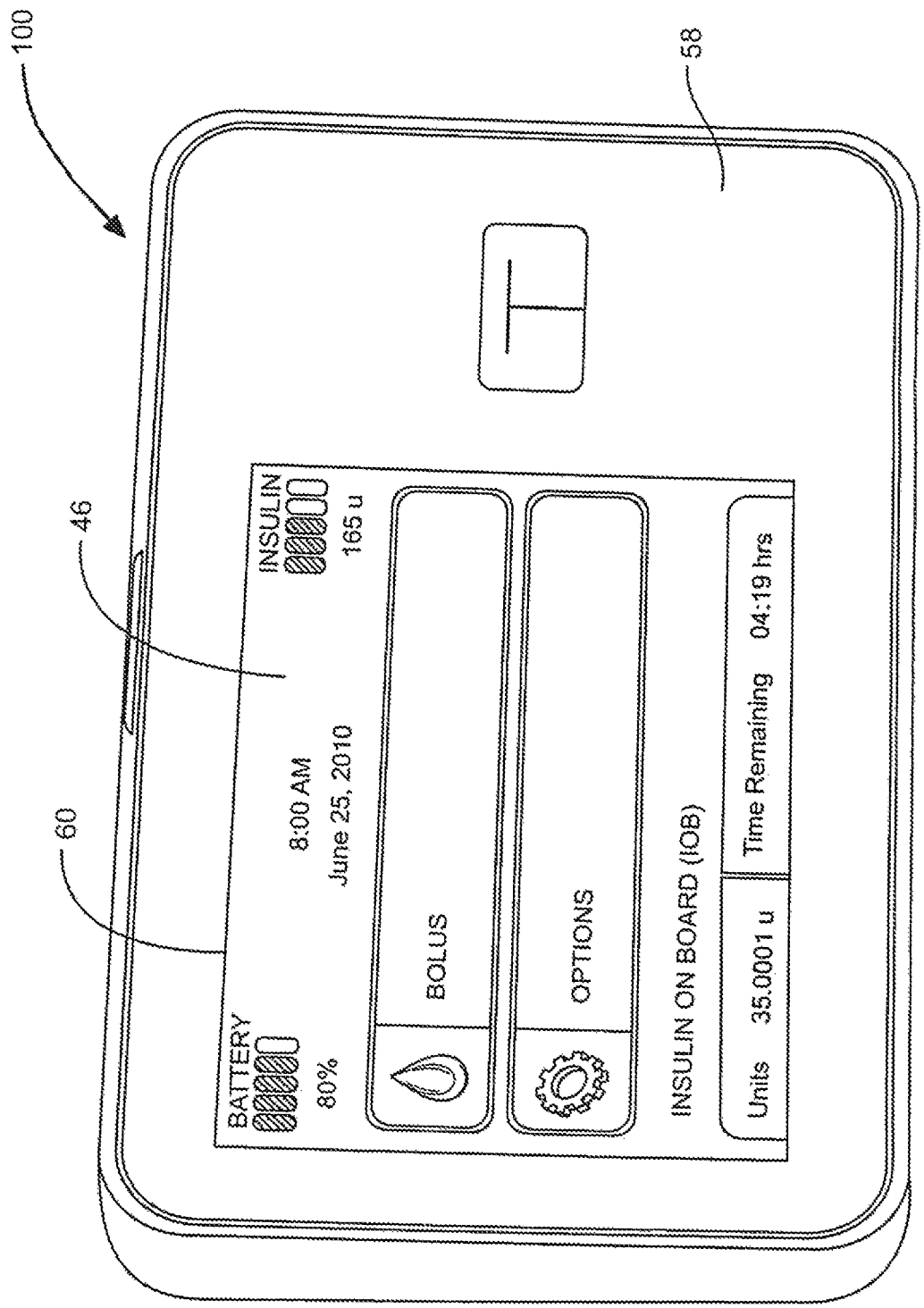
FIG. 3 depicts a screen shot of a home screen page of a graphical user interface of an infusion pump according to an embodiment of the present invention.

Referring to FIG. 3, a front view of the pump 12 is depicted. The pump 12 may include a user interface, such as, for example, a user-friendly GUI 60 on a front surface 58 or other convenient location of the pump 12. The GUI 60 may include a touch-sensitive screen 46 that may be configured for displaying data, facilitating data entry by a patient, providing visual tutorials, as well as other interface features that may be useful to the patient operating the pump 12.

In order to simplify the use of the pump 12 for Type II diabetic patients, the device can be designed so that insulin is delivered with minimal patient interaction. In one embodiment, boluses intended to cover carbohydrates consumed at meal times can be automatically delivered in fixed quantities at fixed times. The user therefore can receive the bolus insulin without having to count the carbohydrates in the meals or remember to enter the carbohydrates to initiate a bolus. As noted above, strict accuracy in carbohydrate consumption and corresponding insulin delivery is not generally required for Type II diabetics, and therefore such a simplified system can be employed.

Figure 4:
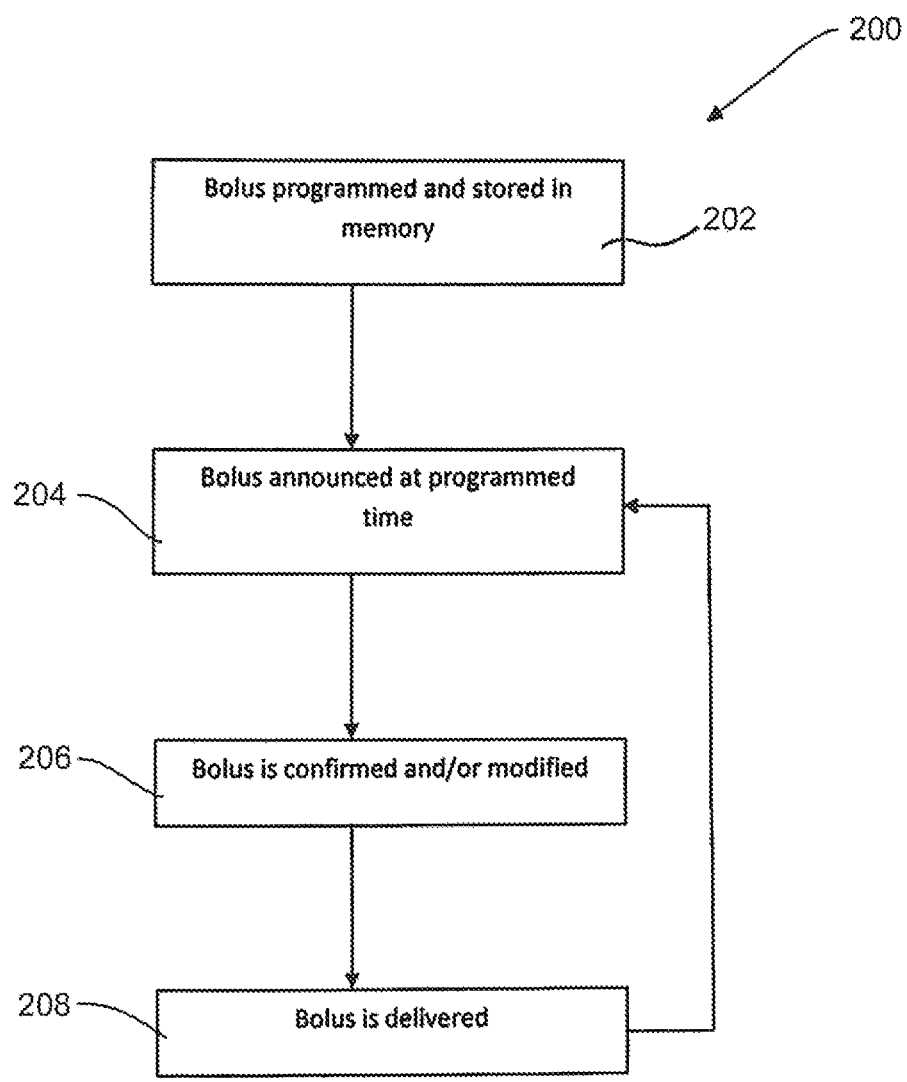
FIG. 4 depicts a flowchart of a method of delivering a bolus of insulin according to an embodiment of the present invention.

FIG. 4 depicts a flowchart of a method of delivering a bolus of insulin 200 according to an embodiment of the present invention. Initially, a bolus is programmed into the pump 12 and saved into memory 30 at step 202. The bolus can be for a fixed amount, such as ten units of insulin, and at a fixed time or time period. The bolus can also be associated with a category of day on which it is to be given, such as on all weekdays or all Mondays. When the fixed time or the beginning of the time period is reached on an associated day, such as 8:00 a.m., the bolus can be announced to the user at step 204. The announcement can comprise an alert including one or more of an audio, visual or tactile indication. Alternatively, the bolus can automatically be delivered without reminding the user.

In some embodiments, the user can confirm the bolus at step 206. Additionally, the user may be able to modify the bolus. Such modifications can include, for example, a change in the volume of the bolus or a delay in delivery of the bolus. The user may also be able to cancel the bolus. If the user confirms the bolus, the bolus is delivered to the user at step 208 and the system reverts to step 204 the next time that the time fixed time or beginning of the time period occurs. Alternatively, the bolus may be automatically delivered to the user following the announcement unless the user positively acts to cancel or change the delivery of the bolus. Thus, rather than the user confirming the bolus to have it delivered, the user must affirmatively cancel the bolus to prevent it from being automatically delivered.

The pump may provide for multiple boluses of the same or different amounts at different times during any given day to be stored in memory. In one embodiment, three boluses are stored for each day, corresponding to an approximate breakfast time, lunch time, and dinner time. Boluses can be stored so that different amounts and/or timing of boluses can be set for weekdays and weekends or for each day of the week. A user may also be able to select a bolus schedule according to certain activities or conditions, such as when the user is sick or has a regularly occurring athletic activity. Thus, once the fixed bolus amounts and times are programmed into the device, no further user interaction with the device is required to determine the timing and amount of bolus deliveries regardless of the timing and size (i.e., number of carbohydrates) of the user's actual meals.

In some embodiments, each bolus can be delivered as an extended bolus. Thus, if the user expects to have lunch around noon on a given day, the bolus can, for example, be delivered as an extended bolus between the hours of 11:00 a.m. and 1:00 p.m. Such an extended bolus therefore helps account for variability in meal times while still being delivered with minimal-to-no user interaction. With such an extended bolus, the user also has the option of editing the bolus while it is being delivered to, for example, add insulin for an increased amount of carbohydrates than usual or decrease or cancel a remainder of the bolus if a smaller than usual meal is eaten. Alternatively, boluses may be delivered all at once at a specified meal time, such as noon. Further detail regarding bolus delivery that can be done with pumps as described herein can found in U.S. patent application Ser. No. 13/800,387 "System and Method for Maximum Insulin Pump Bolus Override" by Walsh.

In another embodiment, the standard meal boluses delivered to the user can be incorporated into a basal rate. Thus, for users that already receive a continuous infusion of insulin as a basal rate, the bolus can be incorporated into that basal rate rather than being delivered in addition to the basal rate around meal times. The user's regular basal rate insulin needs and fixed meal bolus amounts can be combined to calculate an adjusted basal rate that is increased to factor in the meal bolus amounts. Such a protocol ensures the user is receiving enough insulin while further reducing interactions the user must make with the device. As noted herein, such a system is feasible for type II diabetic users because the timing of delivery of insulin relative to meal times is not as critical as with type I users. With such a system, the pump need only be programmed initially and no further user interaction with the device is required until the insulin cartridge needs to be changed with a cartridge having a full insulin reservoir, or if the user desires to change the rate of the insulin being delivered. If the user wishes to modify the new basal rate for any reason, a temporary rate can be delivered.

Some embodiments of an infusion system may include a portable infusion device, as described above and a remote commander device. In such an instance, the portable infusion device may include a suitably configured receiver and/or transmitter for communication with an external device such as a remote commander, as well as programming for directing the use of the device; and the remote commander may additionally include a suitably configured receiver and/or transmitter for communication with an external device such as a portable infusion device, as well as programming for directing the use of the device. For instance, the remote commander may include one or more of the functionalities described herein above with respect to the portable infusion device.

For example, the remote commander may include a processor, a memory, a transmitter and/or receiver, an input mechanism, an output mechanism, e.g., a display, a clock, a timer, an alarm, an estimator, and the like. Hence, in certain embodiments, the portable infusion device may include a transmitter that receives commands, e.g., infusion commands, from the processor and transmits the commands (e.g., to a remote commander or vice-versa). Similarly, the remote commander may include a transmitter that receives commands, e.g., infusion commands, from its processor and transmits the commands (e.g., to a portable infusion device or vice-versa). In such an instance, the portable infusion device and/or remote commander may also include a receiver that receives commands, such as remotely/wirelessly generated commands, and communicates the commands to the processor. Accordingly, the remote commander may include the appropriate hardware and software necessary for producing these functionalities in the remote commander, such as that described above with respect to the portable infusion device. The portable infusion device itself or the remote commander may also include programming that includes an initiating command request, whereby the user has to interact with the device, such as by tapping a screen, e.g., on a display of the portable infusion device or remote commander, so as to accept an infusion recommendation before the remote commander signals the portable infusion device and/or before the portable infusion device accepts the command and begins infusion of the fluid.

Some embodiments of the portable infusion device may also include multiple other capabilities in addition to delivering one or more medicaments (i.e., insulin). For example, the portable infusion device may be capable of interacting with a personal computer (PC) for uploading and downloading data, various file types (e.g., JPEG, PDF) and programs. The portable infusion device may also access and send information wirelessly to a PC or other electronic device (e.g., printer, memory storage device). These functions, for example, may be particularly beneficial to a user for sending and receiving information to a physician, or uploading new or upgrading current programs onto the portable infusion device. Furthermore, the portable infusion device may have instructions, or accessible by the user and/or processor for converting information on the device into various file formats, e.g., portable document format (PDF), word processing documents, JPEG, etc., which may be distributed and shared among various electronic devices. The GUI of the portable infusion device assists in improving the usability of at least these capabilities. In addition, some GUI embodiments may be available to a user by downloading a software application onto the user's cell phone and/or PDA, which would allow the user to use their cell phone or PDA as a remote commander to the portable infusion device.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A method of providing insulin therapy to a user of an ambulatory insulin pump, comprising:
receiving user input defining a meal bolus, the meal bolus comprising a recurring meal bolus of a single fixed amount of all of the insulin configured to counteract an anticipated increase in glucose level as a result of carbohydrates consumed in a meal to be delivered at a predetermined meal time without matching the single fixed amount with a number of carbohydrates consumed in a specific meal;
automatically providing an alert to the user that the meal bolus is scheduled for delivery at the predetermined meal time; and
causing an operation to be initiated to deliver all of the meal bolus to the user with the ambulatory infusion pump in a single continuous delivery operation occurring over a time period including the predetermined meal time.

2. The method of claim 1, further comprising receiving a confirmation in response to the alert and wherein causing an operation to be initiated to deliver all of the meal bolus to the user includes causing the operation to be initiated only after receiving the confirmation.

3. The method of claim 1, further comprising receiving a modification to the meal bolus in response to the alert and wherein causing an operation to be initiated to deliver all of the meal bolus to the user includes causing the operation to be initiated to deliver the meal bolus as modified.

4. The method of claim 1, wherein causing an operation to be initiated to deliver all of the meal bolus to the user includes waiting a predetermined period of time after providing the alert and causing the operation to be initiated if the delivery is not cancelled by the user within the predetermined period of time.

5. The method of claim 1, further comprising associating the recurring meal bolus with a category of day.

6. The method of claim 1, wherein the single continuous delivery operation delivers the meal bolus as an extended bolus.

7. The method of claim 1, wherein the single continuous delivery operation delivers all of the meal bolus starting at the predetermined meal time.

8. The method of claim 1, wherein receiving user input defining a meal bolus receives the user input and automatically providing an alert provides the alert with a user interface of the ambulatory insulin pump.

9. The method of claim 1, wherein receiving user input defining a meal bolus receives the user input and automatically providing an alert provides the alert with a user interface of a remote commander configured to remotely control the ambulatory insulin pump.

10. The method of claim 9, wherein the remote commander is a phone.

11. A method of providing insulin therapy to a user of an ambulatory insulin pump, comprising:
storing a meal bolus in memory, the meal bolus comprising a recurring meal bolus of a single fixed amount of all of the insulin configured to counteract an anticipated increase in glucose level as a result of carbohydrates consumed in a meal to be delivered at a predetermined meal time without matching the single fixed amount with a number of carbohydrates consumed in a specific meal; and
causing an operation to be initiated to deliver all of the meal bolus to a user with the ambulatory infusion pump in a single continuous delivery operation occurring over a time period including the predetermined meal time.

12. The method of claim 11, further comprising providing an alert to the user that the meal bolus is scheduled for delivery at the predetermined meal time.

13. The method of claim 12, further comprising receiving a confirmation in response to the alert and wherein causing an operation to be initiated to deliver all of the meal bolus to the user includes causing the operation to be initiated only after receiving the confirmation.

14. The method of claim 12, further comprising receiving a modification to the meal bolus in response to the alert and wherein causing an operation to be initiated to deliver all of the meal bolus to the user includes causing the operation to be initiated to deliver the meal bolus as modified.

15. The method of claim 12, wherein causing an operation to be initiated to deliver all of the meal bolus to the user includes waiting a predetermined period of time after providing the alert and causing the operation to be initiated if the delivery is not cancelled by the user within the predetermined period of time.

16. The method of claim 12, wherein providing an alert provides the alert with a user interface of the ambulatory insulin pump.

17. The method of claim 11, wherein the single continuous delivery operation delivers the meal bolus as an extended bolus.

18. The method of claim 11, wherein the single continuous delivery operation delivers all of the meal bolus starting at the predetermined meal time.

19. The method of claim 11, wherein providing an alert provides the alert with a user interface of a remote commander configured to remotely control the ambulatory insulin pump.

20. The method of claim 19, wherein the remote commander is a phone.

\* \* \* \* \*